(12) United States Patent
Chapman et al.

(10) Patent No.: US 10,143,202 B2
(45) Date of Patent: Dec. 4, 2018

(54) SYNERGISTIC BLENDS OF ANTIMICROBIALS USEFUL FOR CONTROLLING MICROORGANISMS IN INDUSTRIAL PROCESSES

(71) Applicant: Solenis Technologies, L.P., Schaffhausen (CH)

(72) Inventors: John S Chapman, Lincoln University, PA (US); Corinne E. Consalo, New Castle, DE (US)

(73) Assignee: SOLENIS TECHNOLOGIES, L.P., Schaffhausen (CH)

( * ) Notice: Subject to any disclaimer, the term of this patent is extended or adjusted under 35 U.S.C. 154(b) by 0 days.

(21) Appl. No.: 15/706,993

(22) Filed: Sep. 18, 2017

(65) Prior Publication Data

US 2018/0007912 A1    Jan. 11, 2018

Related U.S. Application Data

(62) Division of application No. 14/211,320, filed on Mar. 14, 2014, now abandoned.

(51) Int. Cl.

| | |
|---|---|
| *A01N 59/00* | (2006.01) |
| *A01N 37/02* | (2006.01) |
| *A01N 35/06* | (2006.01) |
| *A01N 65/00* | (2009.01) |
| *A01N 49/00* | (2006.01) |
| *A01N 37/36* | (2006.01) |
| *A01N 37/10* | (2006.01) |
| *A01N 37/04* | (2006.01) |
| *A01N 65/08* | (2009.01) |
| *C12N 1/18* | (2006.01) |
| *C12N 1/16* | (2006.01) |
| *C12N 1/14* | (2006.01) |
| *C12N 1/00* | (2006.01) |
| *C12P 7/06* | (2006.01) |

(52) U.S. Cl.
CPC .............. *A01N 59/00* (2013.01); *A01N 35/06* (2013.01); *A01N 37/02* (2013.01); *A01N 37/04* (2013.01); *A01N 37/10* (2013.01); *A01N 37/36* (2013.01); *A01N 49/00* (2013.01); *A01N 65/00* (2013.01); *A01N 65/08* (2013.01); *C12N 1/005* (2013.01); *C12N 1/14* (2013.01); *C12N 1/16* (2013.01); *C12N 1/18* (2013.01); *C12P 7/06* (2013.01); *Y02E 50/17* (2013.01)

(58) Field of Classification Search
CPC ................................ C12M 1/00; A01N 35/06
USPC ................................ 510/382; 435/161, 165
See application file for complete search history.

(56) References Cited

U.S. PATENT DOCUMENTS

2012/0295320 A1\* 11/2012 Ziegler .................... C12N 1/18
                                                                                 435/161

FOREIGN PATENT DOCUMENTS

| WO | 0106877 A1 | 2/2001 |
|---|---|---|
| WO | 2011088334 A1 | 7/2011 |

OTHER PUBLICATIONS

Hoikyung Kim, et al., "Production and stability of chlorine dioxide in organic acid solutions as affected by pH, type of acid, and concentration of sodium chlorite, and its effectiveness in inactivating Bacillus cereus spores," Food Microbiology, 2008, pp. 964-969, vol. 25, doi:10.1016/j.fm.2008.05.008.

Ministry of Economic Development and Trade of Ukraine Department of Intellectual Property, Office Action in Ukrainian Patent Application No. a 201509822 dated Nov. 7, 2017.

State Intellectual Property Office of the People's Republic of China, Office Action in Chinese Patent Application No. 201480014736.2 dated Dec. 11, 2017.

H. Kim et al., "Production and stability of chlorine dioxide in organic acid solutions as affected by pH, type of acid, and concentration of sodium chlorite, and its effectiveness in inactivating Bacillus cereus spores," Food Microbiology, 25 (2008) pp. 964-969.

\* cited by examiner

*Primary Examiner* — Walter E Webb
(74) *Attorney, Agent, or Firm* — Lorenz & Kopf, LLP

(57) ABSTRACT

The present invention provides a method of controlling bacterial contamination using synergistic interactions of antimicrobials. The invention consists of combinations of chlorine dioxide and organic acid whose combined antimicrobial effect is greater than the sum of their individual activities, i.e., synergistic.

14 Claims, 3 Drawing Sheets

10,143,202 B2

SYNERGISTIC BLENDS OF ANTIMICROBIALS USEFUL FOR CONTROLLING MICROORGANISMS IN INDUSTRIAL PROCESSES

This application claims the benefit of U.S. provisional application No. 61/791,168, filed Mar. 15, 2013, and is a divisional of U.S. Ser. No. 14/211,320 filed Mar. 14, 2014, the entire contents of which are hereby incorporated by reference.

FIELD OF THE INVENTION

The invention relates to synergistic combinations of antimicrobials and methods of their use for the control of microorganisms in industrial processes, materials, or products where their presence is considered undesirable.

BACKGROUND OF THE INVENTION

It is known that the presence of microorganisms in industrial water systems may be a significant problem in industrial processes, causing issues with decreased product yields, product quality, and process efficiency.

The physical presence of microbes may causes problems, such as their growth in biofilms on heat exchanging surfaces where they cause reductions in heat transfer efficiency. The ability of microbes to consume a wide variety of materials may cause reductions in yields, for example, when microbe consuming cellulose cause yield loss in the paper-making industry. In addition, the production of metabolic products by contaminating microbes may cause issues, such as their production of acidic products which may cause product quality issues or contribute to corrosion issues.

However, in some industries microorganisms are used to produce a number of fermentation products, such as industrial grade ethanol, distilled spirits, beer, wine, pharmaceuticals and nutraceuticals (foodstuff that provides health benefits, such as fortified foods and dietary supplements), baking industry and industrial chemicals. In these instances it is desirable to suppress the growth of unwanted microbes and promote the growth of the wanted ones. In this context the unwanted microbes are those which compete for substrate with or produce metabolic products that interfere with the growth of the wanted microbes which are producing the desired end product.

Yeast are commonly used microbes in fermentation processes. One common type of yeast is *Saccharomyces cerevisiae*, the species predominantly used in baking and fermentation. Non-*Saccharomyces* yeasts, also known as non-conventional yeasts, are also used to make a number of commercial products.

Other microorganisms can also be useful in making fermentation products. For example, cellulosic ethanol production, production of ethanol from cellulosic biomass, utilizes fungi and bacteria. Examples of these cellulolytic fungi include *Trichoderma reesei* and *Trichoderma viride*. One example of a bacteria used in cellulosic ethanol production is *Clostridium ljungdahlii*.

Most of the yeast used in distilleries and fuel ethanol plants are purchased from manufacturers of specialty yeasts. The yeast is manufactured through a propagation process. Propagation involves growing a large quantity of yeast from a small lab culture of yeast. During propagation, the yeast are provided with the oxygen, nitrogen, sugars, proteins, lipids and ions that are necessary or desirable for optimal growth through aerobic respiration.

Once at the distillery, the yeast can undergo conditioning. Conditioning is unlike propagation in that it does not involve growing a large quantity from a small lab culture. During conditioning, conditions are provided to re-hydrate the yeast, bring them out of hibernation and allow for maximum anaerobic growth and reproduction. The objective of both propagation and conditioning is to deliver a large volume of yeast to the fermentation tank with high viability, high budding and a low level of infection by other microorganisms.

Following propagation and/or conditioning, the yeast enters the fermentation process. The yeast is combined in an aqueous solution with fermentable sugars. The yeast consumes the sugars, converting them into aliphatic alcohols, such as ethanol.

The fermentation process begins with the preparation of a fermentable carbohydrate. In ethanol production, corn is one possible source of fermentable carbohydrate. Other carbohydrate sources including cereal grains and cellulose-starch bearing materials, such as wheat or milo, could also be substituted. Cellulosic biomass such as straw and cornstalks could also be used. Cellulosic ethanol production has recently received attention because it uses readily available nonfood biomass to form a valuable fuel.

The propagation, conditioning and fermentation processes can be carried out using batch or continuous methods. The batch process is used for small-scale production. Each batch is completed before a new one begins. The continuous fermentation method is used for large-scale production because it produces a continuous supply without restarting every time.

During the propagation, conditioning or fermentation process the mash or the fermentation mixture can become contaminated with other microorganisms, such as spoilage bacteria. These microorganisms compete with the desired species of yeast for fermentable sugars and retard the desired bio-chemical reaction resulting in a lower product yield. They can also produce unwanted chemical by-products, which can cause spoilage of entire fermentation batches.

Producers of ethanol attempt to increase the amount of ethanol produced from one bushel of cereal grains (approximately 56 pounds (25.4 kilograms)). Contamination by bacteria lowers the efficiency of yeast making it difficult to attain or exceed the desired levels of 2.8-2.9 gallons of ethanol per bushel (0.42-0.44 liters per kilogram). Reducing the concentration of bacteria will encourage yeast propagation and/or conditioning and increase yeast efficiency making it possible to attain and exceed these desired levels.

During any of these three processes the yeast can become contaminated with undesirable yeast, bacteria or other undesirable microorganisms. This can occur in one of the many vessels used in propagation, conditioning or fermentation. This includes, but is not limited to, propagation tanks, conditioning tanks, starter tanks, fermentations tanks and piping and heat exchangers between these units.

Bacterial contamination reduces the fermentation product yield in three main ways. First, the sugars that could be available for yeast to produce alcohol are consumed by the bacteria and diverted from alcohol production, reducing yield. Second, the end products of bacterial metabolism, such as lactic acid and acetic acid, inhibit yeast growth and yeast fermentation/respiration, which results in less efficient yeast production. Finally, the bacteria compete with the yeast for nutrients other than sugar.

After the fermentation system or vessel has become contaminated with bacteria those bacteria can grow much more rapidly than the desired yeast. The bacteria compete with the yeast for fermentable sugars and retard the desired bio-chemical reaction resulting in a lower product yield. Bacteria also produce unwanted chemical by-products, which can cause spoilage of entire fermentation batches. Removing these bacteria allows the desired yeast to thrive, which results in higher efficiency of production.

As little as a one percent decrease in ethanol yield is highly significant to the fuel ethanol industry. In larger facilities, such a decrease in efficiency will reduce income from 1 million to 3 million dollars per year.

Some methods of reducing bacteria during propagation, conditioning and fermentation take advantage of the higher temperature and pH tolerance of yeast over other microorganisms. This is done by applying heat to or lowering the pH of the yeast solution. However, these processes are not entirely effective in retarding bacterial growth. Furthermore, the desirable yeast, while surviving, are stressed and not as vigorous or healthy and do not perform as well.

The predominant trend in the ethanol industry is to reduce the pH of the mash (feed stock) to less than 4.5 at the start of fermentation. Lowering the pH of the mash reduces the population of some species of bacteria. However it is much less effective in reducing problematic bacteria, such as lactic-acid producing bacteria or acetic acid producing bacteria. It also significantly reduces ethanol yield by stressing the yeast used for ethanol production.

Another approach involves washing the yeast with phosphoric acid. This method does not effectively kill bacteria. It can also stress the yeast used for ethanol production, thereby lowering their efficiency.

Yet another method is to use heat or harsh chemicals to sterilize process equipment between batches. It is ineffective at killing bacteria within the yeast mixture during production.

Another approach involves the application of chlorine dioxide, an oxidative antimicrobial, generally to the feedstock or recycled waters used in fermentation. Chlorine dioxide is often generated in situ. Very often high levels are used to overcome the negating effects of high organic loads typically seen with oxidative antimicrobials. The chlorine dioxide may be applied at multiple locations in the process, but high levels in the fermentation tank are avoided since high levels may also inhibit yeast. The large volumes of the systems to be treated and the limited capabilities of current chlorine dioxide generating systems often limits the fermentation systems that can be treated with this approach or requires the deployment of multiple generators.

In yet another method, antibiotics are added to yeast propagation, conditioning or fermentation batch to neutralize bacteria. Fermentation industries typically apply antibiotics to conditioning, propagation and fermentation processes. Antibiotic dosage rates range between 0.1 to 3.0 mg/L and generally do not exceed 6 mg/L. However, problems exist with using antibiotics in conditioning, propagation and fermentation. Antibiotics are expensive and can add greatly to the costs of large-scale production. Moreover, antibiotics are not effective against all strains of bacteria, such as antibiotic-resistant strains of bacteria. Overuse of antibiotics can lead to the creation of additional variants of antibiotic-resistant strains of bacteria.

Currently, almost all U.S. biorefining plants utilize an antimicrobial agent and many of them use antibiotics such as virginiamycin. An important product of corn biorefining is dried distillers grains for use as animal feed, and the market for antibiotic-free feed grains is growing. Distillers grain is the grain residue of the fermentation process. Antibiotic residues and establishment of antibiotic-resistant strains is a global issue. These concerns may lead to future regulatory action against the use of antibiotics. It is expected that the FDA will soon form regulations reducing or eliminating antibiotic use in animal feed. Canada has similar concerns regarding antibiotics in distillers grains and most of their production is exported. Europe has already banned the use of antibiotics in ethanol plants where distillers grains are produced for animal feed. In Brazil, operating antibiotic-free is mandatory in plants producing yeast extract for export. Distiller grains sales account for up to 20% of an ethanol plant earnings. Antibiotic concentration in the byproduct can range from 1-3% by weight, thus negating this important source of income In addition, there are other issues to consider when using antibiotics. Mixtures of antibiotics should be frequently balanced and changed in order to avoid single uses that will lead to antibiotic-resistant strains. Sometimes the effective amount of antibiotic cannot be added to the fermentation mixture. For example, utilizing over 2 mg/L of Virginiamycin will suppress fermentation but over 25 mg/L is required to inhibit grown of *Weisella confusa*, an emerging problematic bacteria strain. Overdosing or overuse of antibiotic can stress yeast and impact efficiency or cause regulatory non-compliance.

Industries that employ fermentation for beverages have historically applied hops acid to propagation and fermentation to control unwanted microbes that compete with the yeast for nutrients. With the recent expansion of fuel ethanol, hops acids have been utilized to a minor degree to address unwanted, gram positive microbes. Competition between yeasts and unwanted microbes results yield loss of fuel ethanol as unwanted microbes, primarily *Lactobacillus* and *Acetobacter*, reduce the efficiency of fermentation. In beverage, competing microbes not only reduce efficiency but can alter the aesthetics and taste of the final product.

Organic acid have many applications, including being used as acidifiers, buffers, antioxidants, chelators, synergists, dietary supplements, flavoring agents, preservatives and antimicrobials. The mode of action of organic acid is that the non-dissociated acids penetrate the bacterial cell wall via passive diffusion and disrupt the normal physiology of the cell in two ways: The acids dissociate and therefore lower the internal pH, which is normally close to neutral, impairing the function of the bacteria. The anionic part of the acid that is unable to leave the cell in its dissociated form accumulates within, disrupting metabolic functions and increasing osmotic pressure. A drawback to the use organic acids is the relatively high levels and volumes required when they are used by themselves.

Since small decreases in ethanol yield are highly significant to the fuel ethanol industry, ethanol producers are constantly looking for ways to increase efficiency. The control of microbes is very significant to many other industries as well and the predominant strategy is treatment with antimicrobials. Antimicrobials are used to eliminate, reduce or otherwise control the number of microbes in aqueous systems. However, the use of most antimicrobials will add cost to operations and products and thus more effective ways to achieve microbial control are sought. In addition, many antimicrobials have deficiencies in either their spectrum of antimicrobial action or operational limitations in their manner of application such as lack of temperature stability or susceptibility to inactivation by environmental or chemical factors. Furthermore, in the instance of facilities using chlorine dioxide or other in situ generated antimicrobials, limitations on the volume of antimicrobial able to be produced may be significant.

Therefore, combinations of antimicrobials may be used, and in particular, synergistic combinations of antimicrobials are preferred. Synergistic combinations of antimicrobials can deliver an antimicrobial effect greater than the sum of the individual antimicrobials and thus can provide an improved cost performance over those combinations which are merely additive in terms of antimicrobial efficacy. In addition, synergistic combinations of antimicrobials in which one is an in situ generated antimicrobial may reduce the required volume of antimicrobial and thus increase the maximum size of the system which can be treated.

DESCRIPTION OF THE INVENTION

Figure 1:
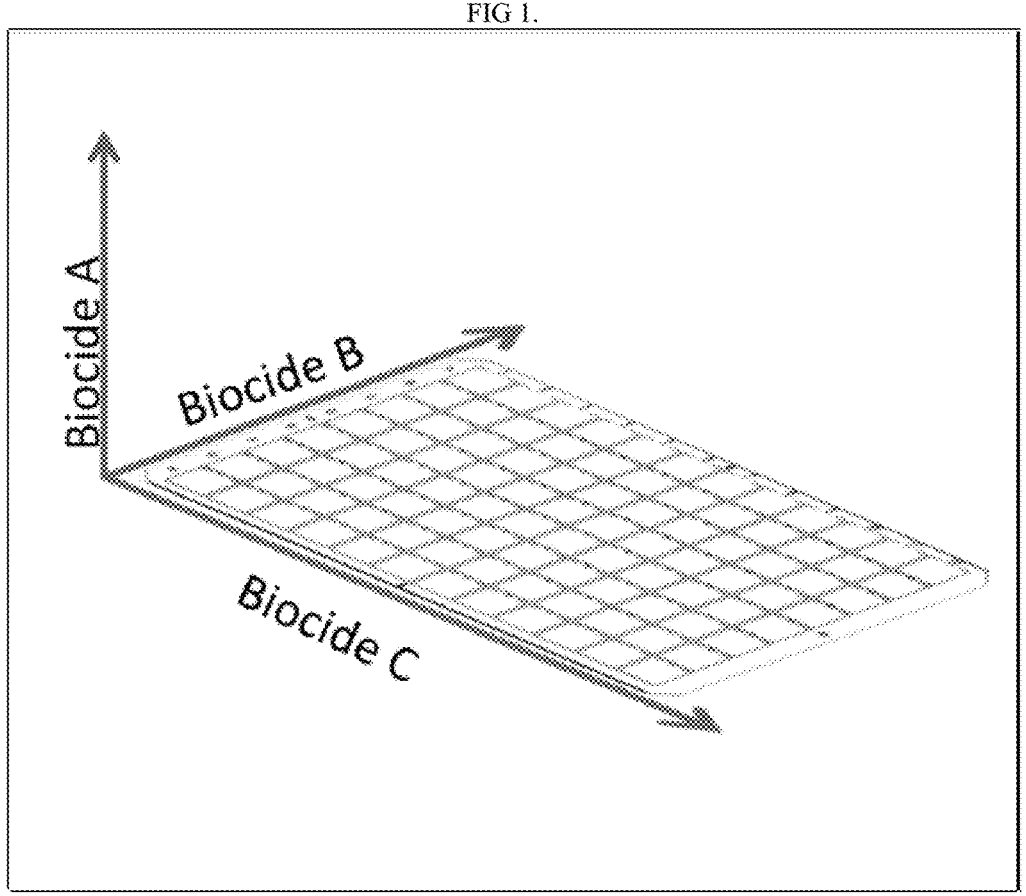
FIG. 1 is a platemap of a ternary checkerboard synergy plate, showing an example of the concentrations of antimicrobials.

For the purposes of this specification, the meaning of "microorganisms" and "microbes" includes, but is not limited to, bacteria, fungi, algae, protozoans, and viruses. Preferred microbes against which these compositions are effective are bacteria, and even more preferred are lactic acid bacteria, acetic acid bacteria, and bacteria which compete for nutrients with yeast in fermentation processes. The microbes can be either aerobic, anaerobic, or facultative with respect to oxygen use. It is also understood that the microbes within water or aqueous systems can be located or suspended within the fluid (eg., planktonic) or localized on a surface in contact with the aqueous system (eg., biofilms). The words and phrases "control", "microbial control", "controlling", and "antimicrobial efficacy" should be broadly construed to include within their meaning, without being limited to, inhibiting the growth of microbes, killing microbes, disinfection, preservation, sanitization, or preventing the re-growth of microbes.

As used herein, ppm is measured as mass per volume, or 1 ppm equals 1 mg (active) per liter. Dosage is defined as the concentration of the component in the system being treated.

As used herein, the term "organic acid" is also referring to its salt. For purposes of the invention the first organic acid is a different organic acid then the second organic acid.

The purpose of the present invention is to achieve a significant reduction of the number of contaminating bacteria in industrial processes, materials, or products where their presence is considered undesirable.

The invention provides a synergistic antimicrobial combination comprising three parts and methods of using the synergistic antimicrobial combination in the control of microorganisms. The composition comprises chlorine dioxide together with hops acids and an organic acid. The composition can comprise chlorine dioxide in conjunction with a first organic acid and a second organic acid where the first organic acid is different from the second organic acid. Preferred organic acids include citric acid, propionic acid, and benzoic acid or their salts. The preferred first organic acid is citric acid. The acids named refer to themselves or their salts.

It has been discovered that these combinations are synergistic in water or aqueous systems when used for microbial control, and are also effective in matrices such as those found in biorefining when corn solids may be present at high levels. Thus, the combined antimicrobial materials result in improved antimicrobial efficacy beyond that which would be expected based on the sum of their individual antimicrobial efficacies. This unexpectedly observed synergy permits reduced amounts of the antimicrobials to be used to achieve acceptable microbial control in industrial processes where water is present.

The present invention provides synergistic antimicrobial combinations comprising chlorine dioxide, hops acid and at least one organic acid and methods of using the combinations of chlorine dioxide, hops acid, and at least one organic acid. The invention also provides synergistic antimicrobial combinations comprising chlorine dioxide, at least one first organic acid and at least one second organic acid and methods of using the combinations of chlorine dioxide, hops acid, and at least one organic acid or the combination of chlorine dioxide, at least one first organic acid and at least one second organic acid. Preferred organic acids include citric acid, propionic acid, and benzoic acid or their salts. The most preferred organic acid is citric acid. The organic acids can be used in their acid form or their salt form. These combinations are useful for controlling microorganisms in aqueous systems and products. The present invention results in a significant reduction of the number of contaminating bacteria in industrial processes, materials, or products where their presence is considered undesirable.

It has been discovered that using the combination of chlorine dioxide, at least one hops acid extract and at least one organic acid or the combination of chlorine dioxide, at least one first organic acid and at least one second organic acid provides synergistic microbial control in aqueous systems. Thus, the combination of components result in improved antimicrobial efficacy beyond that which would be expected based on the sum of their individual antimicrobial efficacies. This unexpectedly observed synergy permits reduced amounts of the antimicrobials to be used to achieve acceptable microbial control in industrial processes, such as biorefining, or materials where desired. In instances in which one antimicrobial is produced in situ such as chlorine dioxide, the reduction in the amount of antimicrobial required allows the combinations to be used in systems whose volume requirements would otherwise be too large to be treated by chlorine dioxide alone.

The composition components may be formulated as a single mixture and added to the system to be treated. They may also be blended after the in situ generation of the chlorine dioxide and added to the system, or they may be added sequentially or at different locations in the process. A person of ordinary skill in the art can readily determine the appropriate method of addition for each system to be treated.

One non-limiting embodiment of the current method for reducing undesirable microorganism concentration in an aqueous system comprises:

(a) introducing chlorine dioxide into the system to be treated, (b) introducing a hops acids into the system to be treated, and (c) introducing at least one organic acid into the system to be treated wherein the chlorine dioxide is at a concentration of at least 1 ppm in the aqueous system to being treated and the concentration of hops acid is at least 0.5 ppm in the aqueous system to be treated. Preferred organic acids include citric acid, propionic acid, and benzoic acid or their salts, most preferred is citric acid or its salt.

Another non-limiting embodiment of the current method for reducing undesirable microorganism concentration in an aqueous system comprises:

(a) introducing chlorine dioxide into the system to be treated,
(b) introducing at least one first organic acid into the system to be treated, and
(c) introducing at least one second organic acid into the system to be treated,
wherein the chlorine dioxide is at a concentration of at least 1 ppm in the aqueous system to being treated and the total concentration of the organic acids (sum concentration of the first organic and the second organic acid) is at least 100 ppm in the aqueous system to be treated. Preferred organic acids include citric acid, propionic acid, and benzoic acid or their salts, most preferred is citric acid or its salt.

The chlorine dioxide used may be generated in situ via a chemical transformation of chlorite or chlorate or other substrate, via electrochemical generation, or may be provided by stabilized formulations of chlorine dioxide.

Non-limiting examples of hops acids that can be used in the invention include beta acid compounds, alpha acids, isomerized alpha acids, rho isomerized alpha acids, tetra isomerized alpha acids, hexa isomerized alpha acids and hop leaf.

Citric acid is the preferred acid useful in the invention but it can reasonably be expected that other organic acids with a similar antimicrobial mechanism would be useful in the present invention. The salts of these acids are also included. Suitable, non-limiting examples of organic acids useful in the present invention include but are not limited to citric acid, benzoic acid, propionic acid, tartaric acid, acetic acid, benzenesulfonic acid, oxalic acid, malic acid, salicylic acid, lactic acid, gluconic acid, hydroxyacetic acid and their salts. For purposes of this invention the organic acid is not a hops acid. Preferred organic acids include citric acid, propionic acid, and benzoic acid or their salts. In systems containing at least one first organic acid and at least one second organic acid, citric acid is the preferred first organic acid.

The chlorine dioxide can be used in amounts of from 1 ppm to 100 ppm in the system to be treated. The chlorine dioxide could be used in amount of from 1 ppm to 75 ppm in the aqueous system to be treated or from 1 ppm to 50 ppm, or from 1 ppm to 15 ppm, or from 3 ppm to 50 ppm, or from 3 ppm to 15 ppm, or from 5 ppm to 20 ppm, or from 5 ppm to 15 ppm. Generally at least 1 ppm or at least 5 ppm or at least 7 ppm of the chlorine dioxide is used. The ratio of the chlorine dioxide to at least one organic acid can be from 1:1 to 1:15,000, or 1:1 to 1:10,000, or ratios of from 1:1 to 1:2000, or ratios of from 1:1 to 1:1000, or ratios of from 1:4 to 1:10,000, or ratios of from 1:4 to 1:2000, or ratios of from 1:4 to 1:1000, or from 1:20 to 1:100. The ratios are based on ppm of material in the aqueous system being treated. Hops acids dosages of at least 0.5 ppm or at least 1 ppm or at least 3 ppm or at least 5 ppm are used. The hops acid dosages can be at least 0.5 ppm and equal to or less than 15 ppm or between 2 ppm and equal to or less than 15 ppm or a dosage of from 3 ppm and 10 ppm or between 5 ppm and equal to or less than 15 ppm or between 5 ppm and 10 ppm can be used in the invention. The ratio of chlorine dioxide to hops acids can be from 100:1 to 1:10, or from 100:1 to 1:5, or from 75:1 to 1:5, or from 75:1 to 1:2, or from 5:1 to 1:5, or 2:1 to 1:2.

One embodiment of the invention comprises citric acid or its salt as the organic acid in combination with chlorine dioxide and hop acids. Preferably there is at least 1 ppm chlorine dioxide and at least 1 ppm hops acid and at least 50 ppm or 75 ppm or 100 ppm citric acid in the system being treated.

One embodiment of the invention comprises propionic acid or its salt as the organic acid in combination with chlorine dioxide and hop acids. Preferably there is at least 1 ppm chlorine dioxide and at least 1 ppm hops acid and at least 50 ppm or 75 ppm or 100 ppm propionic acid in the system being treated.

One embodiment of the invention comprises benzoic acid or its salts as the organic acid in combination with chlorine dioxide and hop acids. Preferably there is at least 1 ppm chlorine dioxide and at least 1 ppm hops acid and at least 50 ppm or 75 ppm or 100 ppm benzoic acid in the system being treated.

In the ternary system comprising chlorine dioxide organic and two organic acids, the organic acids are added to the systems to be treated in the ratios of the first acid to the second acid of from 64:1 up to 1:32, or ratios of from 32:1 to 1:32, or ratios of from 32:1 to 1:16, or ratios of from 8:1 to 1:32, or ratios of from 8:1 to 1:16 or ratios of from 8:1 to 1:8. The first acid can be used in amounts of from 12500 ppm down to 100 ppm in the system to be treated. The first acid could be used in amount of from 6250 down to 100 ppm in the aqueous system to be treated or from 4000 down to 100 ppm or from 4000 down to 200 ppm. Generally at least 100 ppm or at least 200 ppm or at least 300 ppm of the first acid is used. The ratio of the first acid to second organic acid can be from 64:1 to 1:32 or from 32:1 to 1:32 or from 8:1 to 1:32. Generally the sum total amount of the two organic acid used in the system being treated is less than 20,000 ppm, or less than 15,000 ppm or less than 11,000 ppm. Generally the sum total amount of the two acids used in the system being treated is at least 50 ppm or at least 75 ppm or at least 100 ppm. The chlorine dioxide could be used in amount of from 1 ppm to 75 ppm in the aqueous system to be treated or from 1 ppm to 50 ppm or from 1 ppm to 15 ppm or from 3 ppm to 50 ppm or from 3 ppm to 15 ppm of from 3 to 9 ppm. Generally at least 1 ppm or at least 3 ppm or at least 5 ppm or at least 7 ppm of the chlorine dioxide is used in the aqueous system being treated. The ratio of the chlorine dioxide to the total amount of the two organic acids can be from 1:1 up 1:15,000 or ratios of from 1:1 to 1:10000 or ratios of from 1:1 to 1:2000 or ratios of from 1:1 to 1:1200 or ratios of from 1:4 to 1:15,000 or ratios of from 1:4 to 1:10000 or ratios of from 1:4 to 1:2000 or ratios of from 1:4 to 1:1000 or ratios of from 1:20 to 1:100. The first organic acid and the second organic acid are not the same organic acid nor its respective salt. The preferred organic acid for the first organic acid is citric acid or its salt.

Examples of water and aqueous systems in which the compositions are useful are biorefining, cooling water, boiler water, pulp and paper mill water, oil and gas field injection water and produced water, oil and gas pipelines and storage systems, fuel, ballast water, wastewater, pasteurizers, other industrial process water, metalworking fluids, latex, polymers, paint, coatings, adhesives, inks, personal care and household products, reverse osmosis systems, electrochemical deposition systems, fluids used in mineral extraction, mineral slurries, agricultural processing, biorefining waters, and systems that use them. In addition, the compositions may be used in other areas where microbial contamination of water and aqueous systems is required. Such applications include washing fruits and vegetables during processing, and the treatment of waters used in food processing such as their use in tunnel pasteurizers.

The composition components can be combined and then added to the system to be treated. They may also be added sequentially, from a single dosing point, or from separate dosing points. The components of the composition can be added to the water or aqueous system separately or blended prior to addition. A person of ordinary skill in the art can readily determine the appropriate method of addition. The composition can be added to the water or aqueous system with other additives such as, but not necessarily restricted to, surfactants, scale and corrosion control compounds, ionic or non-ionic polymers, pH control agents, and other additives used for altering or modifying the chemistry of the water or aqueous system. In addition, the compositions may be used in water and aqueous systems which contain antimicrobial agents other than those listed herein as synergistic The pH of the aqueous system to be treated is generally from 3 to 11, or from 3 to 7, or from 4 to 9, or from 4 to 8, or from 4 to 6.5, or from 4.5 to 6. In general, the organic acids work best in systems where the pH of the system is less than at least one of the pKa values of the acid or its salt.

In some non-limiting embodiments, the synergistic aqueous solution is comprised of chlorine dioxide and hops acid extracts and citric acid or its salt where the hops acid to organic acid is in ratios of 1:10 to 1:6500, or 1:25 to 1:6400, or 1:25 to 1:1600, or from 1:25 to 1:500 or from 1:25 to 1:100

In some non-limiting embodiments, the synergistic aqueous solution is comprised of chlorine dioxide and hops acid extracts and propionic acid or its salt where the hops acid to organic acid is in ratios of 1:12.5 to 1:800, preferably 1:12.5 to 1:400, preferably from 1:12.5 to 1:50 or 1:10 to 1:6500, or 1:25 to 1:6400, or 1:25 to 1:1600, or from 1:25 to 1:500.

In one embodiment the synergistic aqueous solution is comprised of chlorine dioxide and hops acid extracts and the organic acid is citric acid or its salt. Citric acid could be used in an amount of 1000 ppm down to 50 ppm or from 800 down to 75 ppm or from 600 down to 100 ppm in the aqueous system to be treated. Generally at least 50 ppm or at least 75 ppm or at least 100 ppm of citric acid is used in the aqueous system to be treated. The amount of chlorine dioxide used in the aqueous system to be treated is from 1 ppm to 50 ppm, or from 1 ppm to 15 ppm or from 1 ppm to 10 ppm or from 5 ppm to 10 ppm, and the more preferred composition has 5 to 10 ppm chlorine dioxide or from 3 to 9 ppm chlorine dioxide.

The invention provides synergistic antimicrobial combinations and methods of using them in the control of microorganisms, for example in industrial fermentations producing ethanol or other chemicals.

When used in a fermentation system the combination of chlorine dioxide and hops acid extract and organic acid, preferably citric acid, can be added in various locations in the fermentation system, including the slurry tank(s), cookers, mash coolers, propagators and fermentation tanks. One skilled in the art may also determine other addition points.

In fermentation systems using the present method, the concentrations of bacteria and other undesirable microorganisms can be reduced while propagation and/or conditioning of desirable microorganisms is encouraged. It has been discovered that chlorine dioxide in combination with at least one hops acid extract and at least one organic acid, preferably citric acid, or chlorine dioxide in combination with at least one first organic acid, preferably citric acid and at least on second organic acid is effective at reducing the concentration of undesirable bacteria and other undesirable microorganisms while simultaneously encouraging propagation and/or conditioning of desirable microorganisms. The combination of these products provides a synergistic, antimicrobial treatment without the use of antibiotics.

One non-limiting embodiment of the current method for reducing undesirable microorganism concentration, promoting desirable microorganism propagation, and increasing desirable microorganism efficiency in an aqueous system comprises:
    (a) introducing a fermentable carbohydrate to an aqueous system,
    (b) introducing at least one yeast or desirable microorganism to the aqueous system, and
    (c) introducing chlorine dioxide and at least one hops acid extract and at least one organic acid to the aqueous system.

The chlorine dioxide and the hops acid extract and the organic acid can be introduced into the aqueous system as a blend, or individually, or any two as a blend and the third individually. Preferably the organic acid is citric acid.

Another non-limiting embodiment of the current method for reducing undesirable microorganism concentration, promoting yeast propagation, and increasing yeast efficiency in an aqueous system comprises:
    (a) introducing a quantity of fermentable carbohydrate to an aqueous system,
    (b) introducing a quantity of yeast to the aqueous system, and
    (c) introducing chlorine dioxide and at least one hops acid extract and at least one organic acid into the aqueous system.

The chlorine dioxide and the hops acid extract and the organic acid can be introduced into the aqueous system as a blend, or individually, or any two as a blend and the third individually. Preferably the organic acid is citric acid.

One non-limiting embodiment of the current method for reducing undesirable microorganism concentration, promoting desirable microorganism propagation, and increasing desirable microorganism efficiency in an aqueous system comprises:
    (a) introducing a fermentable carbohydrate to an aqueous system,
    (b) introducing at least one yeast or desirable microorganism to the aqueous system, and
    (c) introducing chlorine dioxide and at least one first organic acid, preferably citric acid, and at least one second organic acid that is not citric acid to the aqueous system, wherein the concentration of chlorine dioxide in the system being treated is at least 1 ppm or at least 5 ppm or at least 10 ppm and the sum concentration of organic acids is at least 50 ppm or at least 75 ppm.

The chlorine dioxide and the at least one first organic acid and the at least one second organic acid can be introduced into the aqueous system as a blend, or individually, or any two as a blend and the third individually. Citric acid sit he preferred first organic acid Another non-limiting embodiment of the current method for reducing undesirable microorganism concentration, promoting yeast propagation, and increasing yeast efficiency in an aqueous system comprises:
    (a) introducing a quantity of fermentable carbohydrate to an aqueous system,
    (b) introducing a quantity of yeast to the aqueous system, and
    (c) introducing chlorine dioxide and at least one first organic acid, preferably citric acid, and at least one second organic acid to the aqueous system, wherein the concentration of chlorine dioxide in the system being treated is at least 1 ppm or at least 5 ppm or at least 10 ppm and the sum concentration of organic acids is at least 50 ppm or 75 ppm.

The chlorine dioxide and the at least one first organic acid and the at least one second organic acid can be introduced into the aqueous system as a blend, or individually, or any two as a blend and the third individually. Citric acid sit he preferred first organic acid.

The steps of the method can be performed sequentially or in a different order. The components of the antimicrobial system can be brought into contact with the yeast or with the fermentation carbohydrate; or the yeast and the fermentable carbohydrate can be combined and then the components of the antimicrobial system be introduced into the combination of yeast and carbohydrate. The components of the antimicrobial system can be combined together and then added to the aqueous system or they can be added separately to the aqueous system. The aqueous system can be in a continuous process or may be a tank in the case of a batch process.

In the foregoing method, the "undesirable" microorganisms intended to be reduced are those that compete for nutrients with the desirable microorganisms that promote the desired fermentation processes. Unwanted or undesirable microorganisms in fermentation include the lactic acid producing bacteria (LAB) and the acetic acid producing bacteria of which *Lactobacillus* and *Acetobacter* are prominent representatives. Any microbe that competes for the fermentable substrate, denying it to the intended fermenting organism and thus reducing yields can be considered undesirable. In this regard, the chlorine dioxide, organic acid and hops acid extract employed in the present method preferably do not detrimentally affect the growth and viability of desirable, fermentation-promoting microorganisms, but do eliminate or suppress the growth of undesirable microorganisms that interfere with the fermentation process. Moreover, the elimination or suppression of undesirable microorganisms has a favorable effect on the growth and viability of desirable microorganisms.

The chlorine dioxide in conjunction with at least one organic acid, preferably citric acid and hops acids can also be used in the treatment of water used to wash fruits and vegetables. Although chlorine dioxide is used in some cases by itself to wash fruits and vegetables, the presence of high organic matter loads often requires high concentrations of chlorine dioxide to be efficacious. Generally the fruit and vegetables are washed by spraying or submerging the fruit or vegetables in an aqueous solution of the antimicrobials, where the concentrations of the antimicrobials are those described above. The synergistic combination of chlorine dioxide, at least one organic acid, preferably citric acid, and hops acids means that a greater antimicrobial effect can be achieved with reduced antimicrobial levels. Another application of chlorine dioxide, a at least one organic acid, preferably citric acid, and hops acids would be in the production of water used to prepare processed food or drinks, or in food hygiene applications like the maintenance of wash water in tunnel pasteurizers. Generally, chlorine dioxide in conjunction with at least one organic acid, preferably citric acid, and hops acids can be used for any application in which the breakdown of the antimicrobial agents produces only salt, water, and a food additive is a desirable result.

The production of fuel ethanol by yeast fermentation is used as an example of where the present invention can be used. Other fermentation products which could employ the combination of the chlorine dioxide in conjunction with the two organic acids or combination of the chlorine dioxide in conjunction with the organic acid, preferably citric acid, and hops acid could include distilled spirits, beer, wine, pharmaceuticals, pharmaceutical intermediates, baking products, nutraceuticals (foodstuff that provides health benefits, such as fortified foods and dietary supplements), nutraceutical intermediates, industrial chemical feedstocks, and enzymes. The current method could also be utilized to treat yeast used in the baking industry.

*Saccharomyces* yeasts are one type of useful yeast such as *Saccharomyces cerevisiae*. Non-*Saccharomyces* yeasts can also be used in the invention. Yeast are not the only beneficial microorganisms used in fermentation. Additional desirable fermenting microorganisms could also be used and benefited by the invention such as the fungi and bacteria typically used in cellulosic ethanol production. Some non-limiting examples of desirable fermenting microorganisms include, but are not limited to, *Trichoderma reesei*, *Trichoderma viride*, and *Clostridium ljungdahlii*.

The components of the antimicrobial system (chlorine dioxide in conjunction with the hops acid extract and at least one organic acid, preferably citric acid, or chlorine dioxide in conjunction with at least one first organic acid, preferably citric acid, and at least one second organic acid) can be added at various points in the propagation, conditioning and/or fermentation processes. The components of the antimicrobial system can be added to cook vessels, fermentation tanks, propagation tanks, conditioning tanks, starter tanks or during liquefaction. The components of the antimicrobial system can also be added directly to the corn mash. The components of the antimicrobial system can also be added to the interstage heat exchange system or heat exchangers. The components of the antimicrobial system can also be added to the piping between these units or heat exchangers.

The components of the antimicrobial system can be added directly into the fermentation mixture. This can be done by adding the components of the antimicrobial system in conjunction with the yeast or other desirable microorganism and fermentable carbohydrate, for example during the SSF (Simultaneous saccharification and fermentation) stage. The dosage is the concentration of the component in the aqueous system being treated. The chlorine dioxide dosages of between 1 and 100 ppm or 1 to 75 ppm or 1 to 50 ppm and the hops acid extract dosages of between 0.5 and 20 ppm or 0.5 to 15 ppm, or from 1 to 10 ppm and the organic acid, preferably citric acid, dosage of between 75 and 1,000 can be added directly into the fermentation mixture. For the antimicrobial system with chlorine dioxide and two organic acids, the chlorine dioxide dosage would be between 1 and 100 ppm or 1 to 75 ppm or 1 to 50 ppm and the sum total of the two organic acids would be at least 50 ppm upto 2000 ppm, preferably citric acids is one of the two acids.

The chlorine dioxide in conjunction with the hops acid extract and at least one organic acid, preferably citric acid, can also be added to the mash prior to the fermentation process. The chlorine dioxide dosages of between 1 and 100 ppm or 1 to 75 ppm or 1 to 50 ppm and the hops acid extract dosages of between 0.5 and 20 ppm or 0.5 to 15 ppm, or from 1 to 10 ppm and the organic acid dosage of between 75 and 1,000 can be added directly into the fermentation mixture. The chlorine dioxide in combination with at least one first organic acid, preferably citric acid, and at least on second organic acid can also be added to the mash prior to the fermentation process. For the antimicrobial system with chlorine dioxide and two organic acids, the chlorine dioxide dosage would be between 1 and 100 ppm or 1 to 75 ppm or 1 to 50 ppm and the sum total of the two organic acids would be at least 50 ppm up to 2000 ppm The chlorine dioxide in conjunction with the hops acid extract and at least one organic acid, or chlorine dioxide in conjunction with the at least one first organic acid extract and at least one second organic acid can also be added during propagation and/or conditioning. For example the chlorine dioxide in conjunction with the hops acid extract and organic acid can be added to the yeast slurry before SSF replacing an acid washing step.

The antimicrobial systems of the present invention, namely chlorine dioxide in conjunction with hops acid and at least one organic acid or chlorine dioxide in combination with at least one first organic acid and at least on second organic acid, can be used to achieve improved results in the production of cellulosic ethanol. Cellulosic ethanol is a type of ethanol that is produced from cellulose, as opposed to the sugars and starches used in producing carbohydrate based ethanol. Cellulose is present in non-traditional biomass sources such as switch grass, corn stover and forestry. This type of ethanol production is particularly attractive because of the large availability of cellulose sources. Cellulosic ethanol, by the very nature of the raw material, introduces higher levels of contaminants and competing microorganism into the fermentation process. The antimicrobial systems of the present invention can be used in cellulosic ethanol production to control undesirable microorganisms. The chlorine dioxide dosages of between 1 and 100 ppm or 1 to 75 ppm or 1 to 50 ppm and the hops acid extract dosages of between 0.5 and 20 ppm or 0.5 to 15 ppm, or from 1 to 10 ppm and the organic acid dosage of between 75 and 1,000 can be can be used in the production of cellulosic ethanol. The chlorine dioxide in combination with at least one first organic acid, preferably citric acid, and at least on second organic acid can also be can be used in production of cellulosic ethanol where the chlorine dioxide dosage is between 1 and 100 ppm or 1 to 75 ppm or 1 to 50 ppm and the sum total of the two organic acids would be at least 50 ppm upto 2000 ppm.

There are two primary processes of producing alcohol from cellulose. One process is a hydrolysis process that utilizes fungi, as for example *Trichoderma reesei* and/or *Trichoderma viride*. The other is a gasification process using a bacteria such as *Clostridium ljungdahlii*. The antimicrobial systems of the present invention can be utilized in either process.

In the hydrolysis process the cellulose chains are broken down into five carbon and six carbon sugars before the fermentation process. This is either done chemically or enzymatically.

In the chemical hydrolysis method the cellulose can be treated with dilute acid at high temperature and pressure or concentrated acid at lower temperature and atmospheric pressure. In the chemical hydrolysis process the cellulose reacts with the acid and water to form individual sugar molecules. These sugar molecules are then neutralized and yeast fermentation is used to produce ethanol. The antimicrobial systems of the present invention can be used during the yeast fermentation portion of this method.

Enzymatic hydrolysis can be carried out using two methods. The first is known as direct microbial conversion (DMC). The DMC method uses a single microorganism to convert the cellulosic biomass to ethanol. The ethanol and required enzymes are produced by the same microorganism. The antimicrobial systems of the present invention can be used during the propagation/conditioning or fermentation steps with this specialized organism.

The second method is known as the enzymatic hydrolysis method. In this method cellulose chains are broken down using cellulase enzymes. These enzymes are typically present in the stomachs of ruminants, such as cows and sheep, to break down the cellulose that they eat. The enzymatic method is typically carried out in four or five stages. The cellulose is pretreated to make the raw material, such as wood or straw, more amenable to hydrolysis. Next the cellulase enzymes are used to break the cellulose molecules into fermentable sugars. Following hydrolysis, the sugars are separated from residual materials and added to the yeast. The hydrolyzate sugars are fermented to ethanol using yeast. Finally, the ethanol is recovered by distillation. Alternatively, the hydrolysis and fermentation can be carried out together by using special bacteria or fungi that accomplish both processes. When both steps are carried out together the process is called sequential hydrolysis and fermentation (SHF).

The antimicrobial systems of the present invention can be introduced for microbiological efficacy at various points in the enzymatic method of hydrolysis. The antimicrobial systems of the present invention can be used in the production, manufacture and fermentation of cellulase enzymes made by *Trichoderma* and other fungi strains. The antimicrobial systems of the present invention acid can be added in the cellulosic simultaneous saccharification and fermentation phase (SSF). The antimicrobial systems of the present invention can be introduced in the sequential hydrolysis and fermentation (SHF) phase. They could also be introduced at a point before, during or after the fermentation by cellulolytic fungi that create the cellulase enzymes. Alternatively the antimicrobial systems of the present invention can be added during the yeast fermentation phase, as discussed above.

The gasification process does not break the cellulose chain into sugar molecules. First, the carbon in the cellulose is converted to carbon monoxide, carbon dioxide and hydrogen in a partial combustion reaction. Then, the carbon monoxide, carbon dioxide and hydrogen are fed into a special fermenter that uses a microorganism such as *Clostridium ljungdahlii* that is capable of consuming the carbon monoxide, carbon dioxide and hydrogen to produce ethanol and water. Finally, the ethanol is separated from the water in a distillation step. The antimicrobial systems of the present invention can be used as an antimicrobial agent in the fermentation step involving microorganisms such as *Clostridium ljungdahlii* that are capable of consuming carbon monoxide, carbon dioxide and hydrogen to produce ethanol and water.

In one non-limiting embodiment, chlorine dioxide, hops acids and at least one organic acid are combined in a tank and diluted to a predetermined concentration at a predetermined ratio. In the tank, chlorine dioxide, hops acid, preferably as isomerized alpha extract, and organic acid, preferably citric acid, are dissolved in water to form a chlorine dioxide/hops acids/organic acid blend. The concentration of the chlorine dioxide solution, the hops acid extract solution and the organic acid solution in the batch tank can vary across a wide range. The blended chlorine dioxide/hops acid extract/organic acid solution is then exhausted from the batch tank through an outlet at a specified dosage rate to create a solution of the desired concentration.

In one non-limiting embodiment, chlorine dioxide, at least one first organic acid and at least second organic acid are combined in a tank and diluted to a predetermined concentration at a predetermined ratio. In the tank, chlorine dioxide, at least one first organic acid preferably citric acid, and at least second organic acid, preferably propionic acid or benzoic acid, or their salts, are dissolved in water to form a chlorine dioxide/first organic acid/second organic acid blend. The concentrations of the chlorine dioxide and the organic acids in solution in the batch tank can vary across a wide range. The blended chlorine dioxide/hops organic acids solution is then exhausted from the batch tank through an outlet at a specified dosage rate to create a solution of the desired concentration.

EXAMPLES

The synergy indices reported in the following examples use the following formula, which is a modification of the formula reported in F. C. Kull, P. C. Eisman, H. D. Sylwestrowka, and R. L. Mayer, Applied Microbiology 9:538-541, 1961.

Synergy Index=$Qa/QA+Qb/QB+Qc/QC$ where $Qa$ is the concentration of Antimicrobial A required to achieve complete inhibition of growth of the test microbe when used in combination with Antimicrobials B and C;

$QA$ is the concentration of Antimicrobial A required to achieve complete inhibition of growth of the test microbe when used alone;

$Qb$ is the concentration of Antimicrobial B required to achieve complete inhibition of growth of the test microbe when used in combination with Antimicrobials A and C;

$QB$ is the concentration of Antimicrobial B required to achieve complete inhibition of growth of the test microbe when used alone;

$Qc$ is the concentration of Antimicrobial C required to achieve complete inhibition of growth of the test microbe when used in combination with Antimicrobials A and B;

$QC$ is the concentration of Antimicrobial C required to achieve complete inhibition of growth of the test microbe when used alone.

A synergy index (SI) of 1 indicates the interactions among the antimicrobials is merely additive, a SI of greater than one indicates the antimicrobials are antagonistic with each other, and a SI of less than 1 indicates the antimicrobials interact in a synergistic manner.

While there are various methods known to individuals skilled in the art for measuring levels of antimicrobial activity, in the following examples the endpoint used is known as the Minimal Inhibitory Concentration, or MIC. This is the lowest concentration of a substance or substances which can achieve complete inhibition of growth.

In order to determine the Minimal Inhibitory Concentration, a two-fold dilution series of the antimicrobial is constructed with the dilutions being made in growth media. The dilutions are made in a 96 well microplate such that each well has a final volume of 280 µl of media and antimicrobial. The first well has, for example, a concentration of 1000 ppm antimicrobial, the second 500 ppm, the third 250 ppm, and so forth, with the 12$^{th}$ and final well in the row having no antimicrobial at all and serving as a positive growth control. After the dilution series is constructed the wells receive an inoculum of microbe suspended in growth media such that the final concentration of microbes in the well is ~$5 \times 10^5$ cfu/ml. In these examples the test microbe used is *Lactobacillus plantarum*. The cultures are incubated at an appropriate temperature for 18-24 hours, and the wells scored as positive or negative for growth based on a visual examination for turbid wells. The lowest concentration of antimicrobial which completely inhibits growth (e.g. a clear well) is designated the Minimal Inhibitory Concentration.

In order to determine whether the interaction between three antimicrobials is additive, antagonistic, or synergistic against a target microbe a modification of the MIC method known as the "checkerboard" method is employed using 96 well microplates. A "checkerboard" synergy plate for two antimicrobials uses an 8×8 two-dimensional grid on a single microplate. The ternary synergy method uses a 8×8×8 three-dimensional grid using a stack of 8 microplates. To construct a checkerboard plate, Antimicrobial A is deployed via the growth media. The antimicrobial is dissolved into the growth media and dispensed onto the eight plates; thus each plate has a single concentration of Antimicrobial A. There is a total of 8 plates each containing a different concentration of Antimicrobial A. The second antimicrobial (Antimicrobial B) is deployed using the two-fold serial dilution method used to construct an MIC plate, where each of the eight rows (A-H) is an identical dilution series of decreasing concentrations which terminates after the eighth column. The third antimicrobial (Antimicrobial C) is deployed by adding identical volumes of a single antimicrobial concentration to each column (1-8), with each column getting a different concentration. Thus, Column 1 receives a volume of media plus Antimicrobial C at 1000 µM, column 2 receives a volume of media plus antimicrobial at 500 µM, etc. The result is each well of the 8×8 well grid has a different combination of antimicrobial concentrations, yielding 64 different combinations of Antimicrobial B and C in total, with Antimicrobial A being held constant. Each of the eight plates has identical grids of Antimicrobials B and C but with different concentrations of Antimicrobial A, yielding a total of 512 different combinations of Antimicrobials A plus B plus C. This is effectively an 8×8×8 grid. The 9$^{th}$ and 10$^{th}$ columns of each plate receive no antimicrobial at all, just media, and serve as positive and negative growth controls, respectively. After the checkerboard microplate is constructed, it is inoculated with *Lactobacillus plantarum*, incubated at 37° C., and scored as described for the MIC method. FIG. 1 depicts the checkerboard microplate.

Example 1: Synergy of Chlorine Dioxide with Hops Acids and Citric Acid

Minimal inhibitory concentrations were determined for chlorine dioxide, hops acids and citric acid at pH 5 using the protocol described above with *Lactobacillus plantarum* as the test microbe. Ternary synergy plates were constructed as described, the wells inoculated to a final concentration of ~$5 \times 10^5$ cfu/ml, incubated for 18-24 hours, and then scored visually for growth/no growth. Synergy indices were calculated according to the modified formula described by Kull et al. This example demonstrates that the effect of combining chlorine dioxide, hops acids and citric acid greater than the effect of any of the antimicrobials alone. The amount of chlorine dioxide needed to inhibit bacterial growth is reduced from 54 ppm to 2.75-40 ppm. The concentration of hops acids drops from 5 ppm to a range of 0.625-2.5 ppm and citric acid goes from 6,250 ppm to 78-1250 ppm.

TABLE 1

| Used Alone | | | Used in Combination | | | | |
|---|---|---|---|---|---|---|---|
| ClO2 MIC (QA) ppm | Hops Acid MIC (QB) ppm | Citric Acid MIC (QC) ppm | ClO2 MIC (Qa) ppm | Hops Acid MIC (Qb) ppm | Citric Acid MIC (Qc) ppm | ClO2:Hops Acid:Citric Acid Ratio | SI |
| 54 | 5 | 6250 | 35 | 1.25 | 78 | 28:1:62.4 | 0.91 |
| 54 | 5 | 6250 | 35 | 0.625 | 78 | 56:1:124.8 | 0.79 |
| 54 | 5 | 6250 | 18.8 | 2.5 | 156 | 7.52:1:62.4 | 0.87 |
| 54 | 5 | 6250 | 37.5 | 1.25 | 156 | 30:1:124.8 | 0.97 |
| 54 | 5 | 6250 | 37.5 | 0.625 | 156 | 60:1:249.6 | 0.84 |
| 54 | 5 | 6250 | 20 | 2.5 | 313 | 8:1:125.2 | 0.92 |
| 54 | 5 | 6250 | 40 | 0.625 | 313 | 64:1:500.8 | 0.92 |
| 54 | 5 | 6250 | 21.25 | 2.5 | 625 | 8.5:1:250 | 0.99 |
| 54 | 5 | 6250 | 2.75 | 2.5 | 1250 | 1.1:1:500 | 0.75 |

Example 2: Fermentation Lab Data

Figure 2:
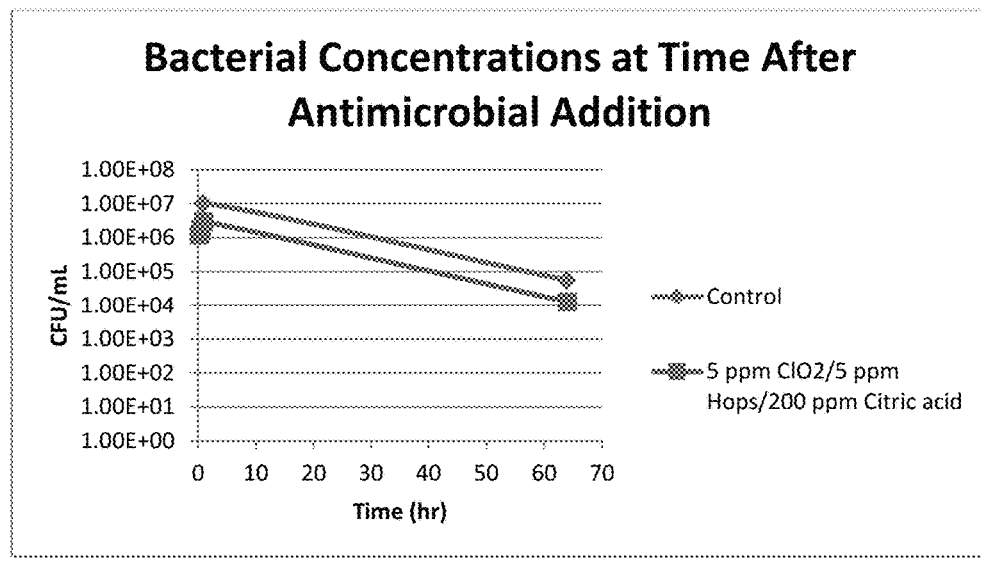
FIG. 2 is a graph depicting the bacterial concentrations at time points after antimicrobial addition and at the end of fermentation (64 hours).

Evaluations were conducted at the National Corn-to-Ethanol Research Center, utilizing chlorine dioxide, hops acid extracts and citric acid. The samples tested and their concentrations can be found in FIG. 2 and Table 2. The tests were conducted to evaluate the effects of ternary antimicrobials on ethanol production in corn mash produced under conditions that are similar to those used in the fuel ethanol industry. Two specific effects were investigated: (1) the ability of antimicrobials to affect ethanol yield and sugar conversion in fermentations that are contaminated by lactic acid bacteria, and (2) the ability of antimicrobials to control bacterial infections compared to control bacteria-free fermentations. Three 160-gram slurries of corn flour, water and enzyme (30% w/w dry solids) were made for each treatment and control (inoculated and uninoculated). The slurries were incubated for 90 minutes at 83° C., cooled to 40° C., and then inoculated with L. plantarum. Next, the slurries were dosed with antimicrobial. The facility dosed chlorine dioxide, hops acid extracts and citric acid to 250-mL Erlenmeyer flasks and samples were collected at 15, 30 and 60 minutes post antimicrobial addition. After the 3 time-point samples were collected, the pH of the mash was adjusted to <5.2 by addition of 300 µl of 5-N sulfuric acid. All enzymes, nutrients, and other amendments added to the fermentation flasks were freshly prepared before use. Urea was added as a sterile 0.2-g/ml solution to a final concentration of 500 ppm (w/w) based on the nitrogen content of the urea (w/w, based on the total mass of mash). The glucoamylase enzyme (Spirizyme Excel, Novozymes) was prepared as a 0.25-g/ml solution and added at a dose of 0.066% (w/w, based on the wet weight of corn). Sterile water was added to equalize the total solids content of each treatment. All fermentation flasks were inoculated with a 0.2-g/ml suspension of yeast (Saccharomyces cerevisiae). This suspension was incubated and mixed for 30 minutes at 40° C. before inoculation into the fermentation flasks. Each fermentation flask was inoculated with 170 µl of the yeast suspension to attain an initial concentration of $1 \times 10^7$ yeast cells/ml. The mass of each flask was recorded after all additions were made, then sanitized fermentation traps were inserted into each flask and they were weighed again. The flasks were incubated at 32° C. with shaking at 170 rpm in an incubator/shaker for a total of 64 hours. Fermentation progress was monitored by weighing the fermentation flasks periodically during the 3-day incubation (at 0, 17.5, 22.5, 42.5, 48, and 64 hrs after inoculation with yeast). The concentrations of substrates (glucose, DP2, DP3, and DP4+, where "DPx" represent glucose oligomers with "x" subunits) and products (ethanol, glycerol, lactic acid, and acetic acid) were measured by HPLC at the end of fermentation. Samples were prepared for HPLC by centrifugation to remove large solids, followed by filtration through 0.45-µm syringe filters, and acidification to pH of approximately 2 by addition of sulfuric acid to a final concentration of 0.01 N. The final pH, concentrations of total dry solids and dissolved dry solids, and the density of the beer filtrate were measured after incubation for 64 hours. Samples from each flask were plated for bacterial colony counts.

TABLE 2

| Time (hours) | Control (CFU/mL) | 5 ppm ClO2/5 ppm hops/200 ppm Citric acid (CFU/mL) |
|---|---|---|
| 0.25 | 1,200,000 | 1,220,000 |
| 0.5 | 1,340,000 | 1,700,000 |
| 1 | 10,300,000 | 3,000,000 |
| 64 | 55,600 | 12,800 |

This example shows that during fermentation, 5 ppm of chlorine dioxide combined with 5 ppm of hops acids combined with 200 ppm of citric acid is effective in reducing bacteria, which was unexpectedly low after seeing the laboratory MIC and synergy data.

Figure 3:
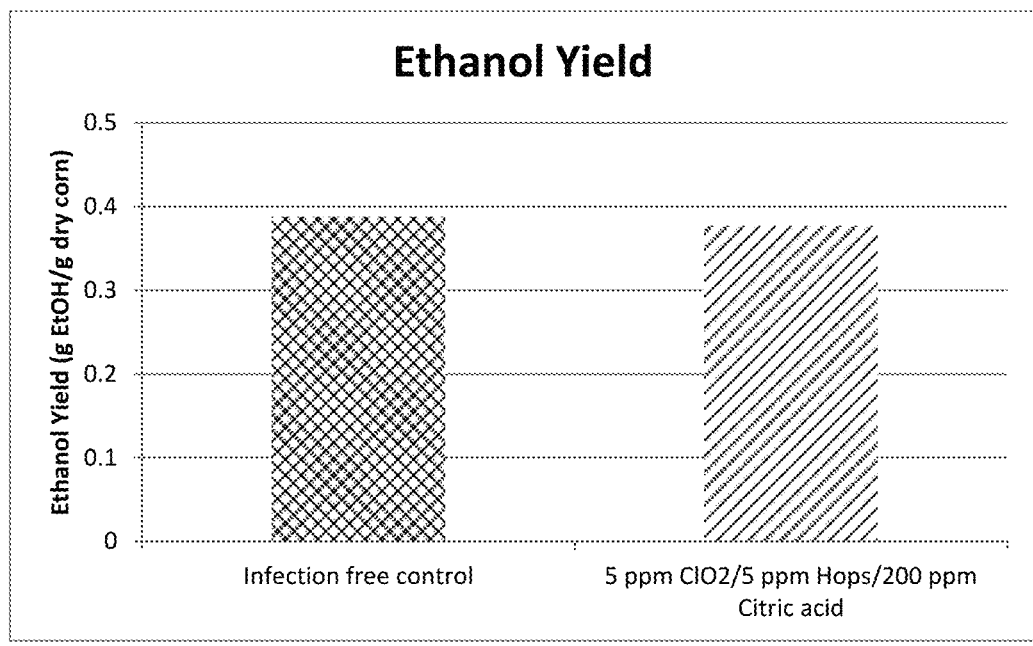
FIG. 3 is a graph depicting the average ethanol yield for treatments expressed as grams ethanol per grams of dry corn.

FIG. 3 and Table 3 show the average ethanol yields of the uninfected control and the three samples after fermentation. No significant differences were observed in the average ethanol yields among all treatments (P=0.769), using ANOVA. In FIG. 3 and table 3 the data represent the average of three independent replicate fermentation flasks.

TABLE 3

| Sample | Ethanol Yield (g ethanol/g dry corn) |
|---|---|
| Infection free control | 0.388 |
| 5 ppm ClO2/5 ppm Hops/200 ppm Citric acid | 0.377 |

The invention claimed is:

1. A method of controlling undesirable microorganism concentration in an aqueous system, the method comprising the steps of:
   (a) introducing chlorine dioxide into an aqueous system,
   (b) introducing an organic acid into the aqueous system,
   (c) introducing an hops acids into the aqueous system,
   wherein the organic acid is selected from the group consisting of citric acid, propionic acid, benzoic acid, and their salts; wherein the concentration of chlorine dioxide is at least 1 ppm in the aqueous system being treated; and wherein the aqueous system is a fermentation system.

2. The method of claim 1 wherein the method further comprising the steps of:
   (x) introducing a fermentable carbohydrate to the aqueous system;
   (y) introducing at least one yeast to said solution.

3. The method of claim 1 wherein the concentration of chloride dioxide is from 1 ppm to 50 ppm in the aqueous system being treated.

4. The method of claim 1 wherein the concentration of chloride dioxide is at least 10 ppm in the aqueous system being treated.

5. The method of claim 3 wherein the concentration of the hops acid is at least 0.5 ppm to 20 ppm, and wherein the concentration of the at least one organic acid is at least 50 ppm to 5000 ppm in the aqueous system being treated.

6. The method of claim 1 wherein the ratio of chlorine dioxide to at least one organic acid is from 1:1 to 1:15,000.

7. The method of claim 1 wherein at least one organic acid comprises citric acid or its salt.

8. The method of claim 7 wherein the ratio of chlorine dioxide to at least one organic acid is from 1:1 to 1:1000.

9. The method of claim 8 wherein the ratio of chlorine dioxide to at least one organic acid is from 1:4 to 1:1000.

10. The method of claim 1 wherein the at least one organic is propionic acid or its salt, and a ratio of chlorine dioxide to at least one organic acid is from 1:1 to 1:1000.

11. The method of claim 1 wherein the at least one organic acid is benzoic acid or its salt, and the ratio of chlorine dioxide to benzoic acid is from 1:1 to 1:32,000, and the concentration of chlorine dioxide is from 1-50 ppm in the aqueous system being treated.

12. The method of claim 1 wherein the at least one hops acid is selected from the group consisting of beta acid compounds, alpha acids, isomerized alpha acids, rho isomerized alpha acids, tetra isomerized alpha acids, hexa isomerized alpha acids and hop leaf or combination thereof.

13. The method of claim 1 wherein the undesirable microorganisms comprise *lactobacillus*.

14. The method of claim 1 wherein the aqueous system further comprises a microorganism that produces alcohol.

* * * * *